(12) United States Patent
Numajiri et al.

(10) Patent No.: US 9,237,845 B2
(45) Date of Patent: Jan. 19, 2016

(54) OPHTHALMOLOGIC IMAGE PICKUP APPARATUS AND CONTROL METHOD THEREFOR

(71) Applicant: CANON KABUSHIKI KAISHA, Tokyo (JP)

(72) Inventors: Yasuyuki Numajiri, Kawasaki (JP); Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/736,257

(22) Filed: Jan. 8, 2013

(65) Prior Publication Data

US 2013/0182219 A1    Jul. 18, 2013

(30) Foreign Application Priority Data

Jan. 16, 2012    (JP) ................. 2012-006011

(51) Int. Cl.
| | |
|---|---|
| A61B 3/14 | (2006.01) |
| A61B 3/113 | (2006.01) |
| A61B 3/117 | (2006.01) |
| A61B 3/12 | (2006.01) |
| A61B 3/10 | (2006.01) |

(52) U.S. Cl.
CPC ............ *A61B 3/113* (2013.01); *A61B 3/1025* (2013.01); *A61B 3/117* (2013.01); *A61B 3/12* (2013.01)

(58) Field of Classification Search
CPC ................................ A61B 3/12; A61B 3/14
USPC ............................ 351/205, 206, 208, 221, 246
See application file for complete search history.

(56) References Cited

U.S. PATENT DOCUMENTS

| 4,830,483 | A |   | 5/1989 | Kohayakawa et al. |
| 4,856,891 | A |   | 8/1989 | Pflibsen et al. |
| 4,866,243 | A |   | 9/1989 | Sakane et al. |
| 5,125,730 | A | * | 6/1992 | Taylor et al. ............ 351/206 |
| 5,894,337 | A |   | 4/1999 | Okinishi et al. |
| 5,943,115 | A |   | 8/1999 | Ferguson |

(Continued)

FOREIGN PATENT DOCUMENTS

| CN | 101103902 A | 1/2008 |
| EP | 0279589 A1 | 8/1988 |

(Continued)

OTHER PUBLICATIONS

May 23, 2013 Great Britain Official Action in Great Britain Patent Appln. No. 1300609.3.

(Continued)

*Primary Examiner* — Mahidere Sahle
(74) *Attorney, Agent, or Firm* — Fitzpatrick, Cella, Harper & Scinto

(57) ABSTRACT

Provided is an ophthalmologic image pickup apparatus for measuring movement of an eye to be inspected at higher speed than a conventional one. The ophthalmologic image pickup apparatus for acquiring an image of an eye to be inspected based on return light from the eye to be inspected which is irradiated with measuring light via a scanning unit, includes: a position acquiring unit for acquiring a plurality of positions of characteristic portions in the image of the eye to be inspected based on the return light from the eye to be inspected corresponding respectively to a plurality of scanning lines of the scanning unit in the image of the eye to be inspected; and a measuring unit for measuring movement of the eye to be inspected based on the plurality of positions.

13 Claims, 13 Drawing Sheets

(56) References Cited

U.S. PATENT DOCUMENTS

| | | | |
|---|---|---|---|
| 6,192,269 B1 | 2/2001 | Okumura et al. | |
| 6,324,420 B1 | 11/2001 | Kishida et al. | |
| 6,337,993 B1 | 1/2002 | Kishida et al. | |
| 6,454,722 B1 | 9/2002 | Numajiri et al. | |
| 6,699,198 B2 | 3/2004 | Numajiri | |
| 6,834,202 B2 | 12/2004 | Ono | |
| 7,533,990 B2 | 5/2009 | Hideshima et al. | |
| 8,098,278 B2 | 1/2012 | Yumikake et al. | |
| 8,308,297 B2 | 11/2012 | Hirose et al. | |
| 8,827,453 B2 | 9/2014 | Nakajima et al. | |
| 2007/0252951 A1* | 11/2007 | Hammer et al. | 351/221 |
| 2008/0002151 A1 | 1/2008 | Hideshima et al. | |
| 2010/0118132 A1 | 5/2010 | Yumikake et al. | |
| 2010/0182567 A1* | 7/2010 | Nouchi et al. | 351/208 |
| 2011/0058029 A1 | 3/2011 | Nakajima et al. | |
| 2011/0103655 A1 | 5/2011 | Young et al. | |
| 2011/0134394 A1 | 6/2011 | Srinivasan et al. | |
| 2011/0249236 A1 | 10/2011 | Saito et al. | |
| 2011/0267581 A1 | 11/2011 | Nakajima et al. | |
| 2011/0267583 A1* | 11/2011 | Hayashi | 351/206 |
| 2011/0301455 A1 | 12/2011 | Numajiri et al. | |
| 2012/0002166 A1 | 1/2012 | Tomatsu et al. | |
| 2012/0154747 A1 | 6/2012 | Makihira | |
| 2012/0229761 A1* | 9/2012 | Makihira | 351/206 |
| 2012/0229762 A1 | 9/2012 | Makihira | |
| 2012/0229763 A1 | 9/2012 | Suehira et al. | |
| 2012/0229764 A1 | 9/2012 | Tomatsu et al. | |
| 2012/0229765 A1 | 9/2012 | Makihira | |
| 2012/0327365 A1 | 12/2012 | Makihira | |
| 2013/0070988 A1 | 3/2013 | Makihira | |
| 2013/0176532 A1* | 7/2013 | Sharma et al. | 351/206 |

FOREIGN PATENT DOCUMENTS

| | | |
|---|---|---|
| EP | 2172149 A1 | 4/2010 |
| EP | 2 347 701 A1 | 7/2011 |
| JP | 2010-227610 A | 10/2010 |
| JP | 2011-056069 A | 3/2011 |
| JP | 2011-229834 A | 11/2011 |
| WO | 2011/111851 A1 | 9/2011 |

OTHER PUBLICATIONS

Jul. 30, 2014 Chinese Official Action in Chinese Patent Appln. No. 201310014807.6.

Nov. 12, 2015 German Official Action in German Patent Appln. No. 102013200290.4.

* cited by examiner

US 9,237,845 B2

OPHTHALMOLOGIC IMAGE PICKUP APPARATUS AND CONTROL METHOD THEREFOR

BACKGROUND OF THE INVENTION

1. Field of the Invention

The present invention relates to an ophthalmologic image pickup apparatus and a measuring method, and more particularly, to an ophthalmologic image pickup apparatus and a control method therefor for measuring movement of an eye to be inspected by using an image of the eye to be inspected.

2. Description of the Related Art

In recent years, as an apparatus for taking an image of an eye to be inspected, there has often been used an ophthalmologic image pickup apparatus which takes an image of the eye to be inspected by scanning the eye to be inspected with measuring light, such as an optical coherence tomography (OCT) capable of acquiring a three-dimensional image, and a confocal scanning laser opthalmoscope (SLO) for acquiring a high resolution moving image. Such an ophthalmologic image pickup apparatus needs some time from start of taking an image until the end thereof, and hence it is vulnerable to the influence of involuntary eye movement, eye movement due to poor fixation, or eye movement due to face movement. Therefore, it is more important to track the eye movement.

As a method of tracking the eye to be inspected, U.S. Pat. No. 4,856,891 discloses a tracking method involving radiating a rectangular tracking beam to a target blood vessel on the fundus, and detecting reflection light of the tracking beam by two orthogonal lines on a two-dimensional sensor so as to measure two-dimensional movement of the fundus. In addition, U.S. Pat. No. 5,943,115 discloses a tracking technology involving radiating a tracking beam that scans a characteristic portion of the fundus in a circular manner, and measuring two-dimensional movement of the fundus based on a phase of the reflection light. However, in the methods in these documents, an additional optical system for tracking is necessary, and eye rotation cannot be detected. Therefore, Japanese Patent Application Laid-Open No. 2011-56069 discloses a technology in which a template image that is a small area image having a feature is extracted from a fundus observation image, and movement of the fundus is measured by pattern matching of searching for a portion that is most similar to the template image.

Here, the technology disclosed in Japanese Patent Application Laid-Open No. 2011-56069 performs the two-dimensional image processing, and hence it takes time to measure the movement of the eye to be inspected.

SUMMARY OF THE INVENTION

It is an object of the present invention to measure movement of an eye to be inspected in an ophthalmologic image pickup apparatus using an SLO at higher speed than a conventional one.

According to an exemplary embodiment of the present invention, there is provided an ophthalmologic image pickup apparatus for acquiring an image of an eye to be inspected based on return light from the eye to be inspected which is irradiated with measuring light via a scanning unit, the ophthalmologic image pickup apparatus including: a position acquiring unit for acquiring plurality of positions of characteristic portions in the image of the eye to be inspected based on the return light from the eye to be inspected corresponding respectively to a plurality of scanning lines generated by the scanning unit in the image of the eye to be inspected; and a measuring unit for measuring movement of the eye to be inspected based on the plurality of positions respectively in the images of the eye to be inspected.

According to the exemplary embodiment of the present invention, the movement of the eye to be inspected can be measured at higher speed than the conventional one.

Further features of the present invention will become apparent from the following description of exemplary embodiments with reference to the attached drawings.

DESCRIPTION OF THE EMBODIMENTS

Embodiments for carrying out the present invention are described in detail with reference to the attached drawings.

(First Embodiment)

A first embodiment of the present invention is hereinafter described.

In this embodiment, a fundus image of an eye to be inspected (an example of the image of the eye to be inspected) is acquired, and intersection positions between a plurality of scanning lines of measuring light scanning the eye to be inspected (for example, a line beam) and a plurality of blood vessels (an example of the characteristic portion of the eye to be inspected) are acquired. Then, movement of the eye to be inspected is measured based on the acquired positions. Note that, the present invention is not limited to the fundus image pickup apparatus for taking an image of the fundus of the eye to be inspected, but can be applied to any ophthalmologic image pickup apparatus that can take an image of the eye to be inspected.

(Entire Structure of Apparatus)

Figure 1:
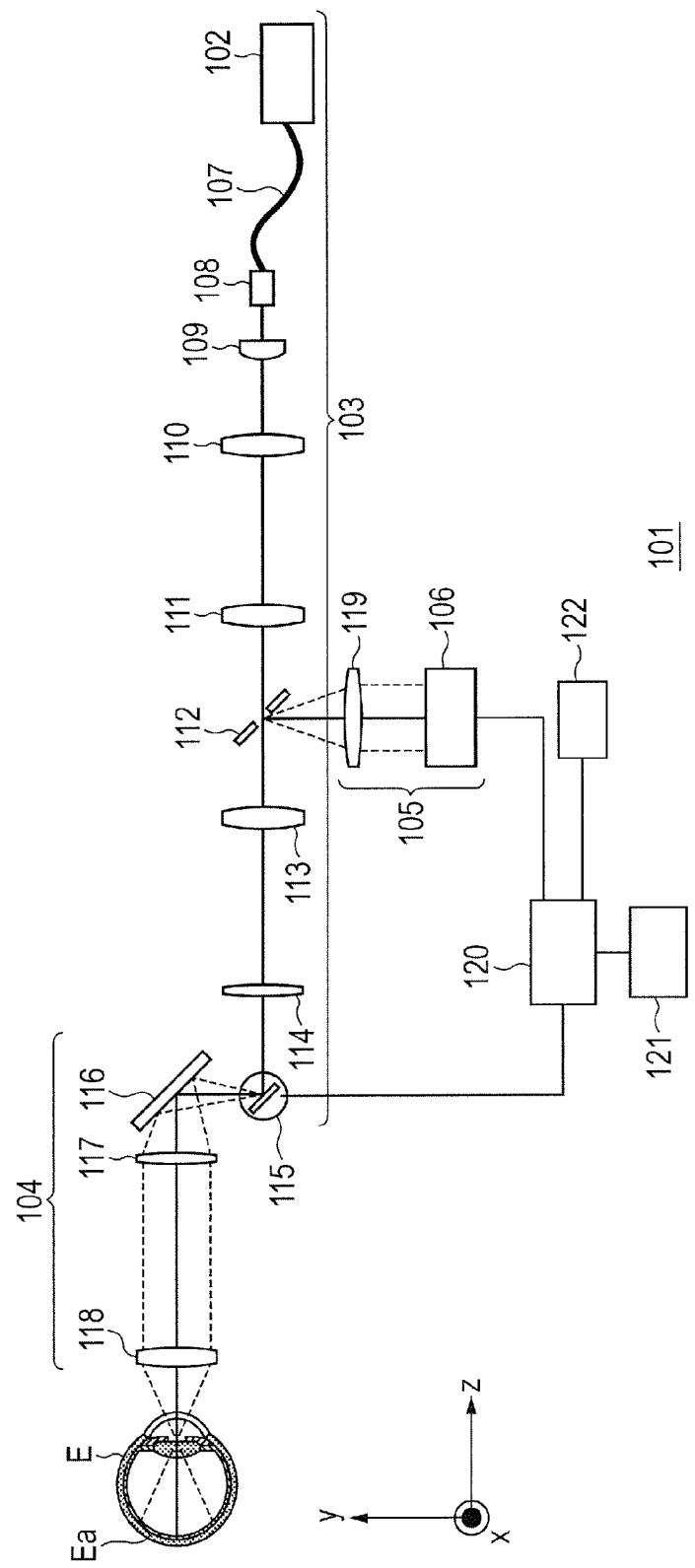
FIG. 1 is a schematic diagram of a structure of a fundus image pickup apparatus according to a first embodiment of the present invention.

A structure of the fundus image pickup apparatus of this embodiment is described with reference to FIG. 1.

In this embodiment, there is used a line SLO (LSLO) apparatus which is an SLO that radiates a linear light beam to the fundus. In an LSLO apparatus 101, illumination light from a light source 102 illuminates a fundus Ea of an eye to be inspected E through optical members of an illumination optical system 103 and an ocular optical system 104. Then, an image of reflected or scattered light as return light from the fundus Ea is formed on a line sensor 106 through parts of the ocular optical system 104 and the illumination optical system 103, and an imaging optical system 105. Thus, the fundus image is acquired. Note that, in FIG. 1, an optical axis direction of the ocular optical system 104 corresponds to a z axis, a direction perpendicular to the z axis in the paper plane corresponds to a y axis, and a direction perpendicular to the paper plane corresponds to an x axis. In addition, the eye to be inspected E in FIG. 1 is viewed from one side, the y axis corresponds to an up and down direction of the eye to be inspected E, and the x axis corresponds to a left and right direction of the eye to be inspected E.

As the light source 102, a semiconductor laser or a super luminescent diode (SLD) light source may be suitable for use. As for the wavelength to be used, in order to reduce glare for a subject and maintain the resolution at the time of fundus observation, a near-infrared wavelength region ranging from 700 nm to 1,000 nm is suitable for use. In this embodiment, a semiconductor laser having a wavelength of 780 nm is used. The laser light emitted from the light source 102 propagates in a fiber 107 and exits from a fiber collimator 108 as a collimated light beam. Then, the collimated light beam enters a cylinder lens 109 (an example of the optical member for shaping the measuring light irradiating the eye to be inspected into a line shape). This cylinder lens 109 is illustrated in a direction different from an actual direction by 90 degrees for description.

The light beam condensed in the x axis direction by the cylinder lens 109 passes through the center of a perforated mirror 112 via relay lenses 110 and 111. The perforated mirror 112 has a center hole and a mirror portion around the hole. After passing through the perforated mirror 112, the light beam passes through relay lenses 113 and 114 and is guided to a scanner 115. As the scanner 115, a galvano scanner is used. Further, the light beam is reflected by a mirror 116, passes through a scan lens 117 and an ocular lens 118, and enters the eye to be inspected E. The light beam entering the eye to be inspected E is radiated to the fundus Ea of the eye to be inspected E as a line beam that is a linear beam. This line beam is reflected or scattered by the fundus Ea of the eye to be inspected E, and propagates along the same optical path so as to return to the perforated mirror 112.

A position of the perforated mirror 112 is conjugate with a pupil position of the eye to be inspected E. Therefore, the light passing through the periphery of the pupil among the reflected or scattered light of the line beam radiated to the fundus Ea is reflected by the perforated mirror 112 and forms an image on the line sensor 106 by a lens 119. Intensity information detected by each element of the line sensor 106 is transmitted to a control portion 120 and is processed so that a fundus image is generated.

The control portion 120 is connected to, in addition to the line sensor 106, the scanner 115, an input device 122 operated by an inspector, and a monitor 121 for displaying the generated fundus image and a display for input operation.

When the control portion 120 controls the scanner 115 to rotate by a very small angle, the line beam scans the fundus Ea in the up and down direction of the eye to be inspected E, namely in the y axis direction so that a two-dimensional fundus image is acquired. The control portion 120 controls the monitor 121 to display the fundus image.

(Eye Movement Measurement)

Figure 2A:
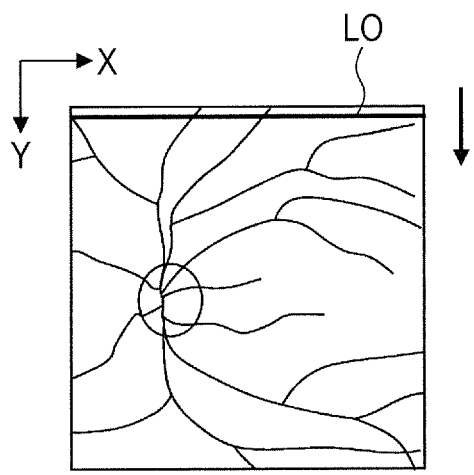
FIG. 2A illustrates an example of a fundus image by LSLO according to the first embodiment.

FIG. 2A illustrates an example of the fundus image acquired as described above. Here, the coordinate axes X and Y are coordinate axes set for the fundus image. The X axis and the Y axis are respectively parallel to the x axis and the y axis of FIG. 1, but have different origins. Symbol L0 represents a line beam radiated to the fundus Ea at a certain timing, which scans the fundus Ea from up to down as illustrated by an arrow in FIG. 2A so that one frame of the fundus image is acquired. This scanning is repeated so that the fundus image is displayed on the monitor 121 (an example of the display portion) in real time. The display is performed by a module region of the control portion 120, which functions as a display control unit for controlling the display portion (display unit) to display the image of the eye to be inspected in real time. In addition, in this case, the scanning line to be a target of the operation process for obtaining the intersection points as described below is displayed in a linear display form of the position corresponding to the scanning line on the displayed image. Designation of a display position thereof on the image of the eye to be inspected is performed by a module region of the control portion 120, which functions as a designation unit.

Figure 2B:
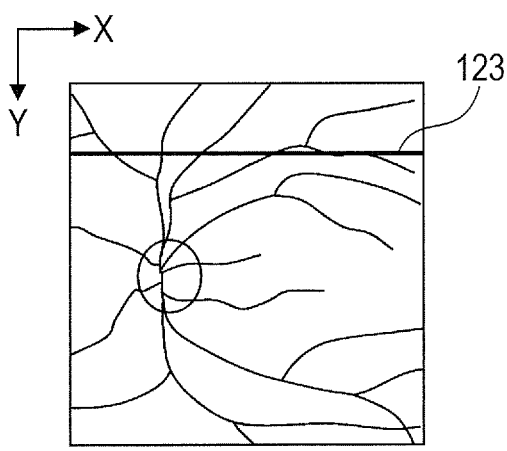
FIG. 2B is an explanatory diagram of procedure.
Figure 3:
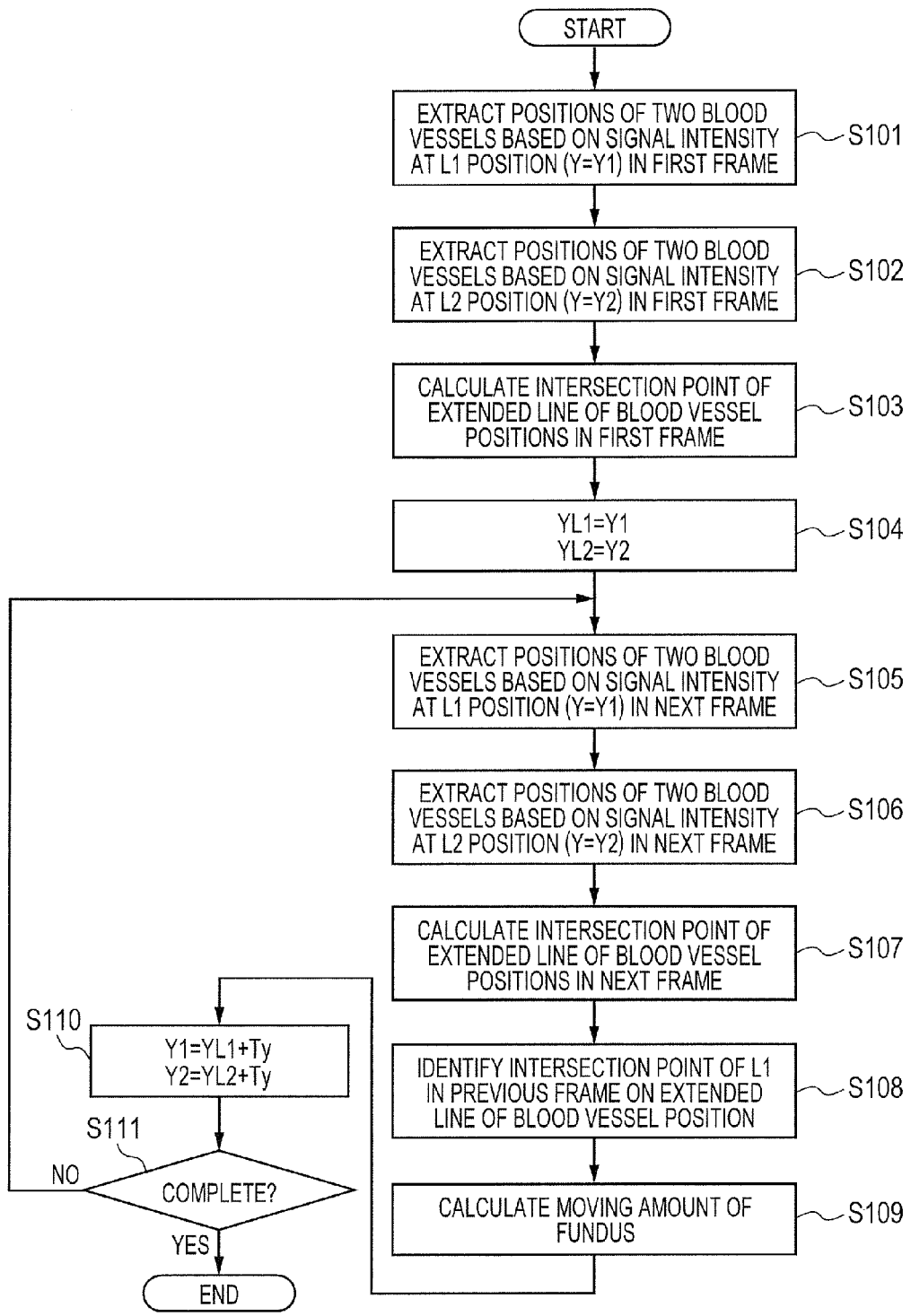
FIG. 3 is a flowchart according to the first embodiment.

As illustrated in FIG. 2B, a cursor 123 that is a line parallel to the X axis is displayed on the fundus image of the monitor 121. The inspector operates the input device 122 while viewing the fundus image so as to move the cursor 123 in the Y axis direction, and designates a position where the cursor 123 crosses a plurality of blood vessels on the fundus, two blood vessels close to the left (having small X values) are not parallel to each other, and the blood vessels do not branch in the vicinity. Note that, two blood vessels close to the left are used in this embodiment, and hence a position where the blood vessels are not parallel to each other (a position of two blood vessels crossing each other) is designated. However, a criterion for selecting the position may be changed in accordance with a method to be used for extracting the blood vessels. The individual blood vessels are respective examples of a first blood vessel and a second blood vessel in the present invention. These blood vessels may be extracted as two blood vessels having different gradients or may be extracted as nonparallel blood vessels whose extended lines cross each other. In addition, blood vessels are used in this embodiment, but the present invention is not limited thereto. It is possible to use any characteristic portions that can be extracted as linear images in various images obtained from the eye to be inspected.

Figure 4A:
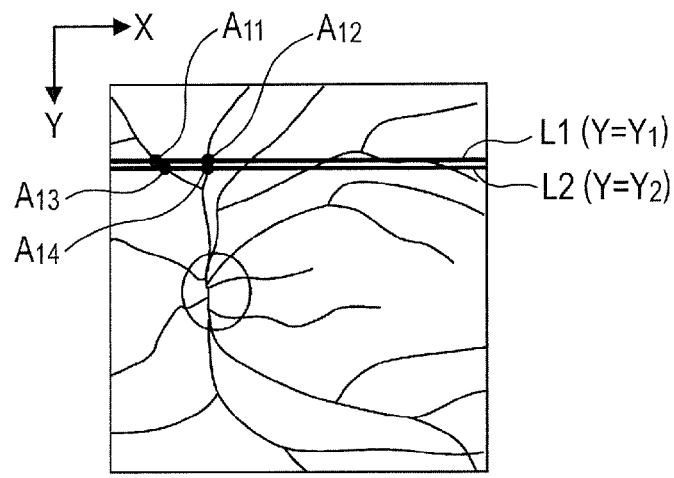
FIGS. 4A, 4B and 4C are explanatory diagrams of procedure according to the first embodiment.
Figure 4B:
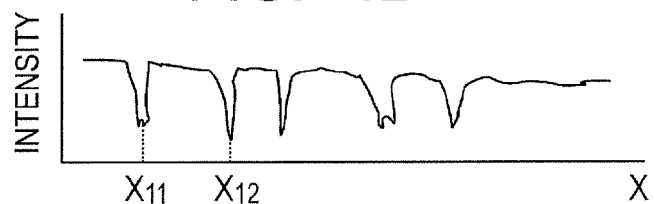

When the cursor 123 is fixed by an input from the inspector, the control portion 120 starts to measure the eye movement. The control portion 120 is a measuring unit for measuring the eye movement. A measurement flow of the eye movement measurement is described. First, a first frame that is the latest frame when the measurement is started, namely data in first area scanning is used. In Step S101, two blood vessels close to the left are extracted based on the signal intensity of the line sensor 106 on a line L1 at the position where the cursor 123 is fixed, namely at $Y=Y_1$, as illustrated in FIG. 4A. Then, X positions of the intersection points between the line and the center portions of the two blood vessels are respectively identified as positions where the individual blood vessels cross the line, namely the scanning line (positions of the blood vessels crossing the scanning line are acquired). The intersection points between the line and the center portions of the two blood vessels are represented by $A_{11}$ and $A_{12}$, and coordinates thereof are expressed by $(X_{11}, Y_1)$ and $(X_{12}, Y_1)$. In this case, the signal intensity of the line sensor 106 is as illustrated in FIG. 4B, in which positions of center portions of the two blood vessels having small X values are identified as $X_{11}$ and $X_{12}$. Note that, because a relatively thick blood vessel having a diameter larger than 100 μm usually has large central specular reflection with high signal intensity, a position of not a minimum value but a maximum value is fetched. In addition, a position of the center portion of the blood vessel is identified in this embodiment, but it is possible to identify an edge of the blood vessel.

Next, in Step S102, as illustrated in FIG. 4A, on a line L2 at a position apart from the line L1, where the cursor 123 is fixed, by 5 pitches in the Y direction, namely on a line $Y=Y_2$, X positions of the intersection points between the line and the same two blood vessels are extracted similarly to Step S101. The intersection points between the line and the center portions of the two blood vessels are represented by $A_{13}$ and $A_{14}$, and coordinates thereof are expressed by $(X_{13}, Y_2)$ and $(X_{14}, Y_2)$. The position of the above-mentioned scanning line L1 corresponds to a first scanning position, the position of the scanning line L2 corresponds to a second scanning position, and the positions $(X_{11}, Y_1), (X_{12}, Y_1), (X_{13}, Y_2)$, and $(X_{14}, Y_2)$ of the blood vessels crossing the scanning lines are first blood vessel positions. In addition, the lines L1 and L2 correspond to the scanning lines in the present invention. The operation of identifying positions at which the blood vessels cross the different scanning lines L1 and L2 (acquiring the positions of the blood vessels intersecting with the scanning lines) from the signal intensity of the line sensor 106 is performed by a module region of the control portion 120 as the measuring unit, which functions as a first blood vessel position acquiring unit or a position acquiring unit. In addition, it is preferred that the above-mentioned distance between the lines in the Y direction be set appropriately. This operation of setting the position of the second scanning line at a position apart from the designated position of the first scanning line by a predetermined distance is performed by a module region of the control portion 120, which functions as a determining unit.

Note that, the height of the line beam on a standard fundus in the Y axis direction is approximately 20 μm. Because a data acquiring pitch for generating an image is 20 μm, 5 pitches correspond to 100 μm.

Figure 4C:
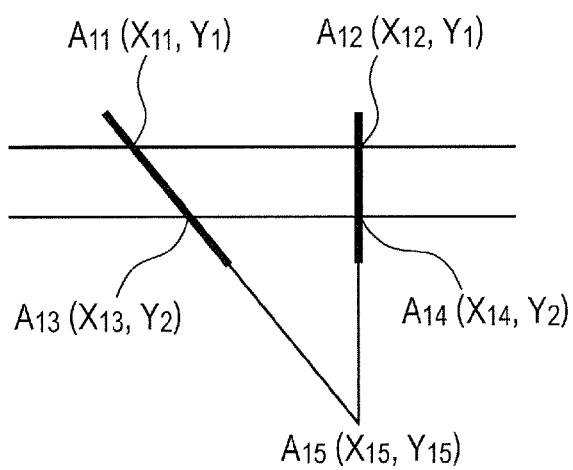

In Step S103, as illustrated in FIG. 4C, based on the above-mentioned intersection points in the first frame, a position of an intersection point $A_{15}$ between an extended line of a line segment $A_{11}$-$A_{13}$ and an extended line of a line segment $A_{12}$-$A_{14}$ is determined. Coordinates of the intersection point $A_{15}$ are expressed by $(X_{15}, Y_{15})$. Then, values $X_{15}$ and $Y_{15}$ can be determined by the following equations using the coordinates of $A_{11}, A_{12}, A_{13}$, and $A_{14}$.

$$X_{15} = \frac{X_{13}X_{12} - X_{11}X_{14}}{(X_{12} - X_{11}) - (X_{14} - X_{13})} \quad (1)$$

$$Y_{15} = \frac{(X_{12} - X_{11})Y_2 - (X_{14} - X_{13})Y_1}{(X_{12} - X_{11}) - (X_{14} - X_{13})} \quad (2)$$

The fundus image of the first frame described above becomes a reference for the tracking to be described below. Therefore, in Step S104, Y coordinate values of the lines L1 and L2 are stored as $YL_1$ and $YL_2$.

$$YL_1 = Y_1 \quad (3)$$

$$YL_2 = Y_2 \quad (4)$$

Figure 5A:
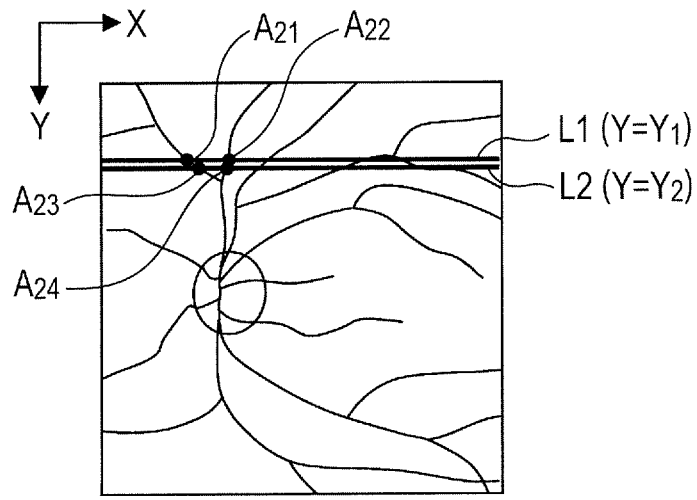
FIGS. 5A and 5B are explanatory diagrams of procedure according to the first embodiment.

From Step S105, data of the next frame, namely the second scanning line that is second area scanning, are handled. The data are obtained from the second fundus image acquired at a time different from a time at which the return light from the eye to be inspected corresponding to the first scanning line for the first fundus image is acquired. As illustrated in FIG. 5A, the fundus image in the next frame is moved from the fundus image in the first frame. In Step S105, at the position of the line L1 ($Y=Y_1$) used in Step S101, namely at the first scanning position, similarly to Step S101, the X positions of intersection points between the line and the center portions of the two blood vessels are identified. The intersection points between the line and the center portions of the two blood vessels are represented by $A_{21}$ and $A_{22}$, and coordinates thereof are expressed by $(X_{21}, Y_1)$ and $(X_{22}, Y_1)$. In this embodiment, because the frame rate is 200 frames per second, the moving amount of the fundus is sufficiently small, and hence the same blood vessels as in Step S101 can be extracted.

In Step S106, similarly to Step S102, at the line L2 illustrated in FIG. 5A, namely at the second scanning position, X positions of intersection points between the line and the two blood vessels are identified. The intersection points between the line and the center portions of the two blood vessels are represented by $A_{23}$ and $A_{24}$, and coordinates thereof are expressed by $(X_{23}, Y_2)$ and $(X_{24}, Y_2)$. The above-mentioned positions $(X_{21}, Y_1), (X_{22}, Y_1), (X_{23}, Y_2)$, and $(X_{24}, Y_2)$ of the blood vessels crossing the lines L1 and L2 are second blood vessel positions. The operation of acquiring the positions of the blood vessels crossing the scanning lines L1 and L2 based on the signal intensity of the line sensor 106, which is obtained by the second area operation, is performed by a module region of the control portion 120 as the measuring unit, which functions as a second blood vessel position acquiring unit or the above-mentioned position acquiring unit.

Figure 5B:
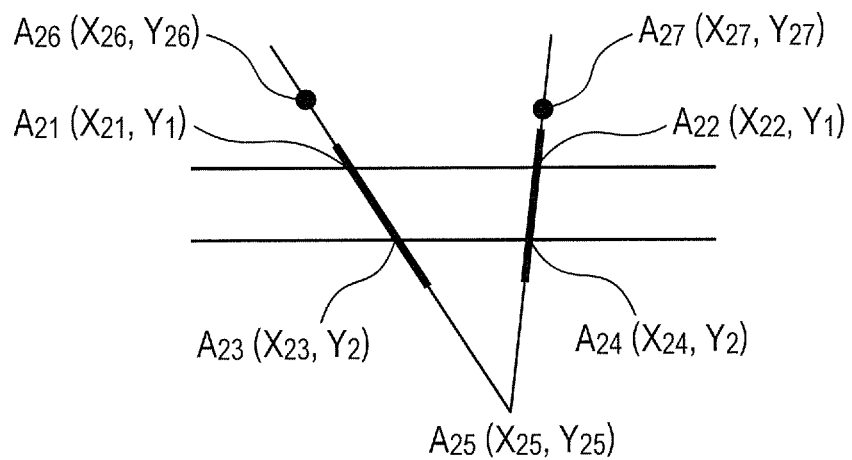

Next, in Step S107, similarly to Step S103, a position of an intersection point $A_{25}$ between an extended line of a line segment $A_{21}$-$A_{23}$ and an extended line of a line segment $A_{22}$-$A_{24}$ illustrated in FIG. 5B is determined. Coordinates of the intersection point $A_{25}$ are expressed by $(X_{25}, Y_{25})$. Then, values $X_{25}$ and $Y_{25}$ can be determined by the following equations using the coordinates of $A_{21}, A_{22}, A_{23}$, and $A_{24}$. This means that the intersection point $A_{15}$ in Step S103 has moved to the intersection point $A_{25}$ by the fundus movement.

$$X_{25} = \frac{X_{23}X_{22} - X_{21}X_{24}}{(X_{22} - X_{21}) - (X_{24} - X_{23})} \quad (5)$$

$$Y_{25} = \frac{(X_{22} - X_{21})Y_2 - (X_{24} - X_{23})Y_1}{(X_{22} - X_{21}) - (X_{24} - X_{23})} \quad (6)$$

In Step S108, in order to identify moved points other than the intersection point $A_{15}$ in Step S103 and the intersection point $A_{25}$ in Step S107, positions which are on the extended lines of the line segment $A_{21}$-$A_{23}$ and the line segment $A_{22}$-$A_{24}$ and which intersect with the line L1 in the previous frame are determined by the following equations. The points are represented by $A_{26}$ and $A_{27}$, and coordinates of the points $A_{26}$ and $A_{27}$ are expressed by $(X_{26}, Y_{26})$ and $(X_{27}, Y_{27})$.

$$X_{26} = X_{25} - (X_{25} - X_{21}) \times \frac{\sqrt{(X_{15} - X_{11})^2 + (Y_{15} - Y_1)^2}}{\sqrt{(X_{25} - X_{21})^2 + (Y_{25} - Y_1)^2}} \quad (7)$$

$$Y_{26} = Y_{25} - (Y_{25} - Y_1) \times \frac{\sqrt{(X_{15} - X_{11})^2 + (Y_{15} - Y_1)^2}}{\sqrt{(X_{25} - X_{21})^2 + (Y_{25} - Y_1)^2}} \quad (8)$$

$$X_{27} = X_{25} - (X_{25} - X_{22}) \times \frac{\sqrt{(X_{15} - X_{12})^2 + (Y_{15} - Y_1)^2}}{\sqrt{(X_{25} - X_{22})^2 + (Y_{25} - Y_1)^2}} \quad (9)$$

$$Y_{27} = Y_{25} - (Y_{25} - Y_1) \times \frac{\sqrt{(X_{15} - X_{12})^2 + (Y_{15} - Y_1)^2}}{\sqrt{(X_{25} - X_{22})^2 + (Y_{25} - Y_1)^2}} \quad (10)$$

As described above, in this embodiment, it is supposed that each of the two blood vessels is a straight line. Because it is supposed that a distance between the lines L1 and L2 is 100 μm and that the frame rate is 200 frames per second, it is no problem to regard the blood vessels as straight lines in consideration of a range for extracting the blood vessels and the eye movement. Note that, if the distance between the lines L1 and L2 is larger, a straight line between the lines can be expressed with higher accuracy, but with deviating from actual running of blood vessels. An appropriate distance value is within the range of 100 to 300 μm.

Next, in Step S109, the moving amount of the fundus, which is the first moving amount here, is calculated. When a point (x, y) is moved to a point (x', y') by a translational movement amount (Tx, Ty) and a rotational movement angle θ, the following determinant is satisfied.

$$\begin{pmatrix} x' \\ y' \end{pmatrix} = \begin{pmatrix} \cos\theta & -\sin\theta \\ \sin\theta & \cos\theta \end{pmatrix} \begin{pmatrix} x \\ y \end{pmatrix} + \begin{pmatrix} Tx \\ Ty \end{pmatrix} \quad (11)$$

Equation (11) is applied to the movements of the three points from $A_{15}(X_{15},Y_{15})$, $A_{11}(X_{11},Y_1)$, and $A_{12}(X_{12},Y_1)$ to $A_{25}(X_{25},Y_{25})$, $A_{26}(X_{26},Y_{26})$, and $A_{27}(X_{27},Y_{27})$, respectively. Because the points determined from the first and second blood vessel positions are used, the first moving amount is calculated based on the first and second blood vessel positions. The method is performed by calculating the translational movement amounts Tx and Ty and the rotational movement angle θ using the method of least squares so that the translational movement amounts Tx and Ty and the rotational movement angle θ become minimum values.

In Step S110, considering the movement amount Ty in the Y direction of the determined translational movement amount as described above, in order to determine intersection points between the lines L1 and L2, and the blood vessel in the next frame, the following equations are satisfied.

$$Y_1 = YL_1 + Ty \quad (12)$$

$$Y_2 = YL_2 + Ty \quad (13)$$

In other words, new lines L1 and L2 apart from the first and second scanning positions by the determined moving amount in the Y direction as described above become third and fourth scanning positions. This corresponds to performing actual tracking of the position of the blood vessels to be extracted only in the Y direction. By the operation described above, the movement of the eye to be inspected is measured by the above-mentioned measuring unit as at least one movement of the translational movement and the rotational movement of the eye to be inspected.

Further, in Step S111, it is determined whether or not there is an input from the inspector to complete the eye movement measurement. When there is an input, the eye movement measurement is completed. When there is not any input, the process returns to Step S105 so as to continue the eye movement measurement.

When Step S105 and subsequent steps are repeated, an image obtained from the next frame, namely a third scanning line by third area scanning is further handled. In this case, first, in Steps S105 to S108, third blood vessel positions are identified, which are positions of the blood vessels crossing the above-mentioned new third and fourth scanning lines L1 and L2, namely the third and fourth scanning positions. The operation of identifying the positions where the blood vessels cross the scanning lines L1 and L2 based on the signal intensity of the line sensor 106, which is obtained by the third area operation, is performed by a module region of the control portion 120 as the measuring unit, which functions as a third blood vessel position acquiring unit.

Next, after calculation is performed in accordance with Equations (5) to (10), the moving amount of the fundus, namely a second movement is calculated based on the positions of the first and third blood vessels using Equation (11) in Step S109.

As described above, in this embodiment, the moving amount can be determined by simple calculation without adding an optical system to the LSLO apparatus. Therefore, it is possible to measure the moving amount of the fundus at high speed. The above-mentioned embodiment relates to the ophthalmologic apparatus for acquiring the fundus image of the eye to be inspected based on the return light from the eye to be inspected, which is return light of the measuring light radiated to the eye to be inspected via the scanner 115 as the scanning unit. In this embodiment, a plurality of positions of the blood vessels present on the scanning line or crossing the scanning line are acquired from the image obtained as the image signal on the line sensor 106 from the plurality of scanning lines obtained when the measuring light scans the fundus by the scanning unit. The acquiring operation is performed by a module region of the control portion 120, which functions as the position acquiring unit. In addition, based on the positions of the plurality of blood vessels obtained by the position acquiring unit, a module region of the control unit 120, which functions as the measuring unit, measures the movement of the eye to be inspected.

(Second Embodiment; OCT Optical System)

A second embodiment of the present invention is hereinafter described.

In this embodiment, similarly to the first embodiment, the fundus image is acquired, and intersection points between a radiation beam and a plurality of blood vessels are extracted. After that, the fundus movement is calculated, and then the positions to be extracted are changed so as to calculate the fundus movement. Then, the fundus movement value is fed back to an optical coherence tomography (OCT) apparatus for the fundus so as to acquire a high quality OCT image (a tomographic image or a three-dimensional image with little positional shift).

(Entire Structure of Apparatus)

A structure of the fundus image pickup apparatus of this embodiment is described with reference to FIG. 6.

A fundus image pickup apparatus 201 of this embodiment is formed of an OCT image pickup portion and an SLO image pickup portion. In other words, this embodiment relates to a structure including the OCT image pickup portion that is an ophthalmologic apparatus having a function different from a function for taking a fundus image. The SLO image pickup portion is used for acquiring a fundus image as an observation image when acquiring a tomographic image or a three-dimensional image of the fundus by the OCT image pickup portion. Each structure is hereinafter described in detail. The SLO image pickup portion is the same as that of the first embodiment except for a part. In FIG. 6, the same components are denoted by the same symbols as those in FIG. 1 of the first embodiment.

Figure 6:
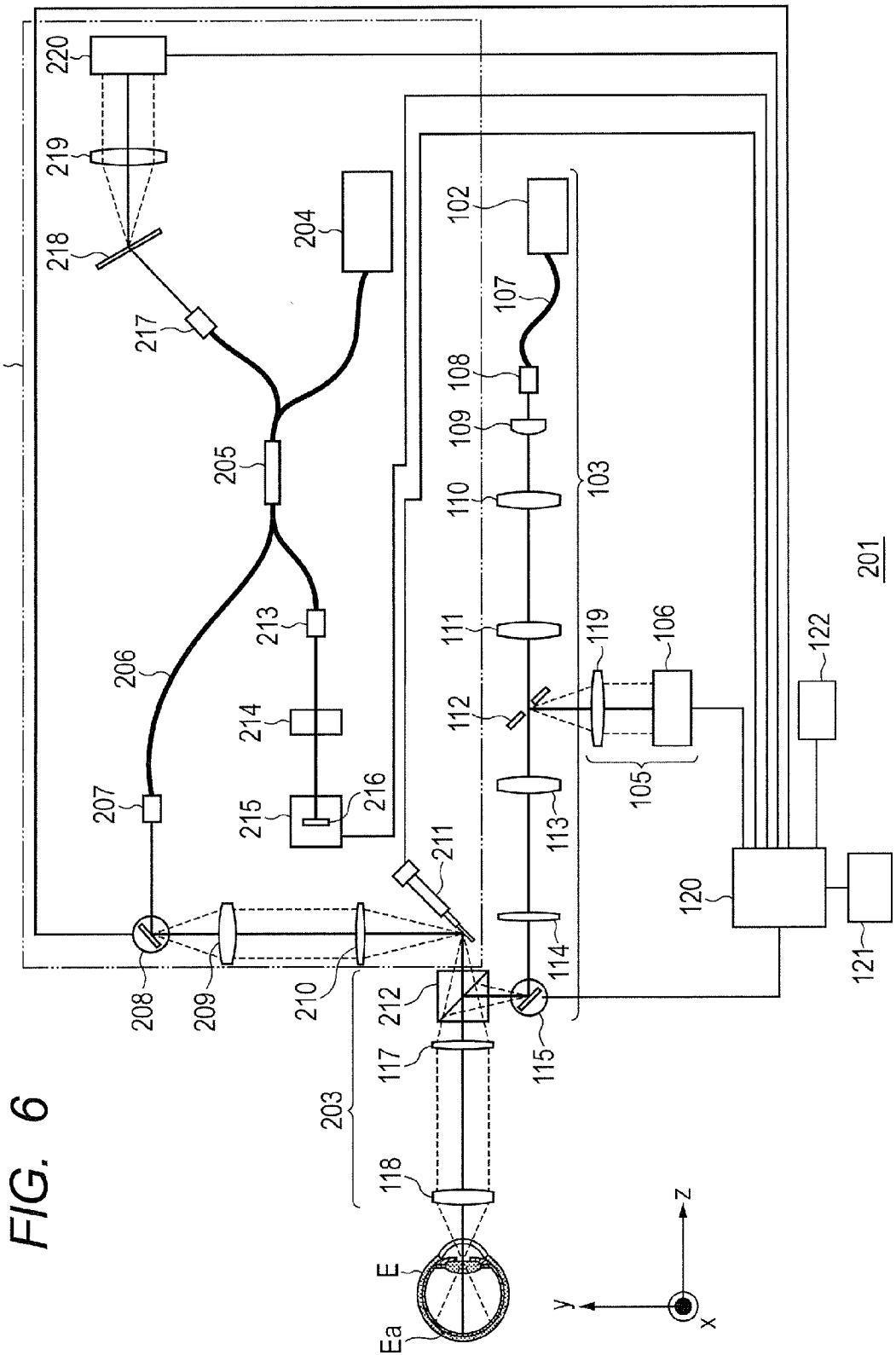
FIG. 6 is a schematic diagram of a structure of a fundus image pickup apparatus according to a second embodiment of the present invention.

The OCT image pickup portion of this embodiment uses a spectral domain method and is formed of an OCT portion 202 enclosed by a double dot dashed line and an ocular optical system 203 in FIG. 6. As a light source 204, a super luminescent diode (SLD) light source of low coherent light is used. As the wavelength thereof, it is preferred to use wavelengths of 850 nm or the vicinity and 1,050 nm or the vicinity to take a fundus image. In this embodiment, an SLD light source having a center wavelength of 840 nm and a wavelength half value width of 45 nm is used.

The low coherent light emitted from the light source 204 propagates in an optical fiber and enters a fiber coupler 205 to be split into measuring light and reference light.

The measuring light propagates in an optical fiber 206 and is radiated as collimated light from a fiber collimator 207. Further, the measuring light passes through a Y direction OCT scanner 208, relay lenses 209 and 210, an X direction OCT scanner 211, a beam splitter 212, the scan lens 117, and the ocular lens 118 so as to enter the eye to be inspected E. Here, as the X direction OCT scanner 211 and the Y direction OCT scanner 208, galvano scanners are used. In addition, the direction of rotating the X direction OCT scanner 211 is an OCT main scanning direction, and the direction of rotating the Y direction OCT scanner 208 is an OCT sub-scanning direction. The measuring light entering the eye to be inspected E is reflected or scattered by the fundus Ea, propagates along the same optical path, and returns to the fiber coupler 205. Note that, the X direction OCT scanner 211 and the Y direction OCT scanner 208 are illustrated in directions different from those in reality for description.

The reference light is guided from the fiber coupler 205 to a fiber collimator 213, and then exits as collimated light. The exiting reference light passes through dispersion correction glass 214, and is then reflected by a reference mirror 216 provided to an optical path length varying stage 215. The reference light reflected by the reference mirror 216 returns to the fiber coupler 205 through the same optical path.

The measuring light and the reference light, which have returned to the fiber coupler 205, are combined by the fiber coupler 205 to generate interference light, and are then guided to a fiber collimator 217. The fiber collimator 217, a grating 218, a lens 219, and a line sensor 220 constitute a spectroscope. The interference light generates intensity information of each wavelength by the spectroscope, and the intensity information is detected by individual elements of the line sensor 220. The intensity information is transmitted to the control portion 120 and is processed. Further, when the control portion 120 controls the X direction OCT scanner 211 and the Y direction OCT scanner 208 to rotate by a very small angle, intensity information is obtained from a target region of the fundus so that a tomographic image of the target region is generated and is displayed on the monitor 121.

Next, a structure of the SLO image pickup portion for acquiring the fundus image is described with reference to the same diagram of FIG. 6. Similarly to the first embodiment, the SLO apparatus used in this embodiment is an LSLO. As the light source 102, it is preferred to use a semiconductor laser or an SLD light source. The wavelength to be used is not limited as long as the wavelength can be separated by the beam splitter 212 from the wavelength of the light source 204 as low coherent light for OCT. However, it is preferred to use a near-infrared wavelength region of 700 to 1,000 nm in view of image quality of the fundus observation image. In this embodiment, a wavelength of 760 nm is used. The laser light emitted from the light source 102 propagates along the same optical path as that in the first embodiment, is reflected by the beam splitter 212, and enters the eye to be inspected E in the same manner. The beam splitter 212 transmits an OCT beam and reflects an SLO beam. Similarly to the first embodiment, the beam having entered the eye to be inspected E is radiated as a linear beam to the fundus Ea of the eye to be inspected E, and is reflected or scattered by the fundus Ea. Then, the beam forms an image on the line sensor 106 in the same manner. The intensity information detected by each element of the line sensor 106 is transmitted to the control portion 120 and is processed so that the fundus image is generated. Note that, the structure described above is an example of a first optical system in the present invention, and the scanners and the like disposed in the optical system constitute the scanning unit in the present invention. In addition, as described later, the first optical system includes an optical member for shaping the measuring light into a line shape.

The control portion 120 is connected to, in addition to the line sensor 106, the scanner 115, the Y direction OCT scanner 208, the X direction OCT scanner 211, the optical path length varying stage 215, and the line sensor 220. Further, the control portion 120 is also connected to the input device 122 for the inspector to perform the input operation, and the monitor 121 for displaying the generated fundus image and a display for the input operation.

When the control portion 120 controls the scanner 115 to rotate by a very small angle, the line beam scans the fundus Ea in the up and down direction of the eye to be inspected E, namely in the y axis direction so that a two-dimensional fundus image is acquired. The control portion 120 controls the monitor 121 to display the fundus image.

(Eye Movement Measurement)

Figure 7:
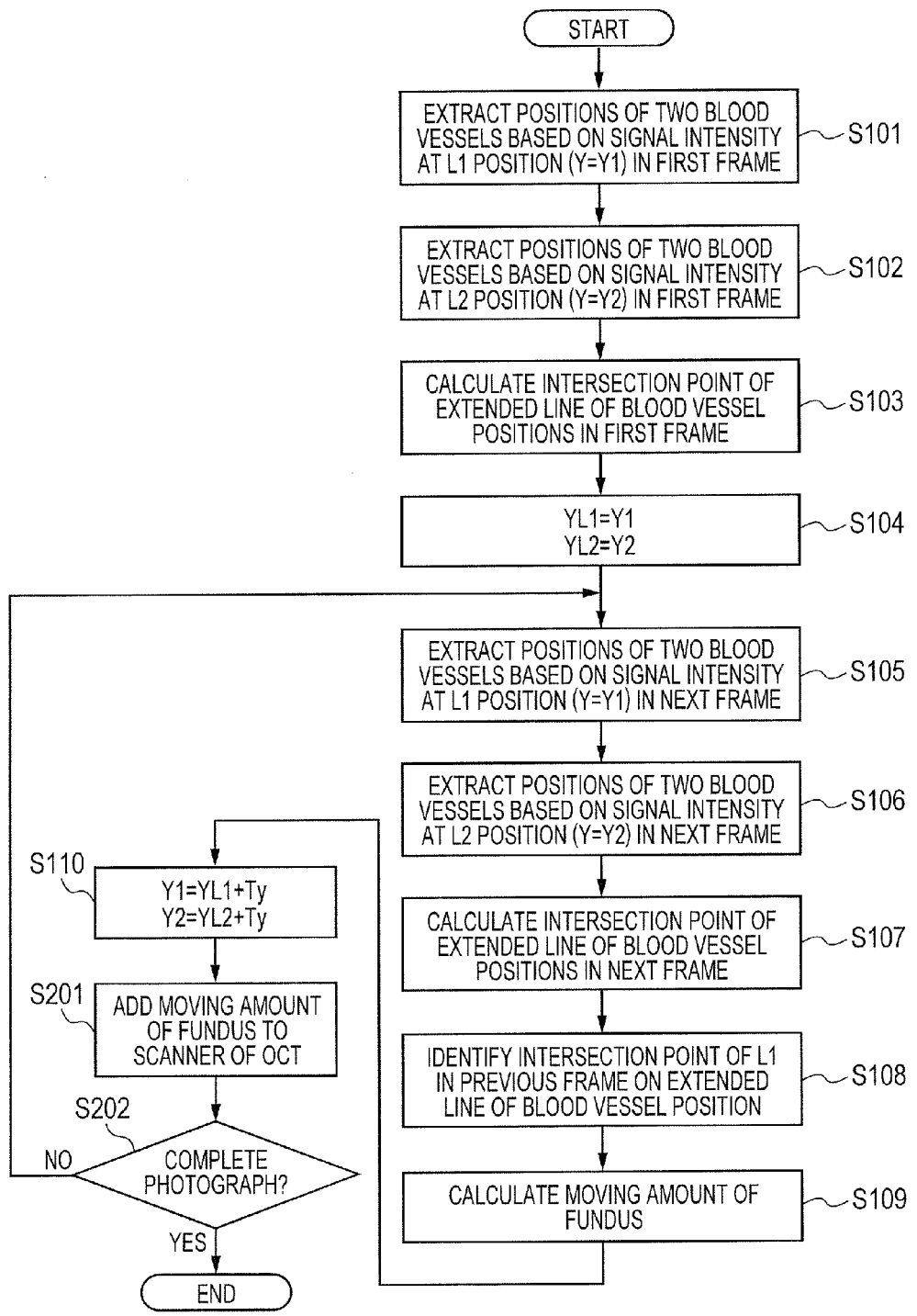
FIG. 7 is a flowchart according to the second embodiment.

Similarly to the first embodiment, when the cursor 123 is fixed by an input from the inspector, the control portion 120 starts to measure the fundus movement. FIG. 7 illustrates an eye movement measurement flow. Steps S101 to S110 are the same as in the first embodiment, and hence description thereof is omitted.

In the next Step S201, the measured eye movement is fed back to the OCT optical system (referred to also as an OCT apparatus). In other words, as an example of the control unit in the present invention, the control portion 120 drives the Y direction OCT scanner 208 and the X direction OCT scanner 211 of OCT after adding the translational movement amounts Tx and Ty and the rotational movement angle θ determined in Step S109. Note that, these scanners are an example of a second scanning unit of the present invention, and the optical system corresponds to the second optical system. The above-mentioned control unit performs a function of feeding back the measured movement of the eye to be inspected to the second scanning unit. Specifically, as the translational movement amounts Tx and Ty, scanning start positions may be shifted respectively by amounts Tx and Ty by controlling rotations of the X direction OCT scanner 211 and the Y direction OCT scanner 208. In addition, as the rotational movement angle θ, an angle θ may be set by controlling rotation of the Y direction OCT scanner 208 in the sub-scanning.

A B-scan image that is an OCT tomographic image usually has a frame rate of 30 to 150 frames per second although depending on a speed of the line sensor and the number of pixels of the image, and the frame rate of the LSLO may correspond thereto.

Further, in Step S202, the OCT image pickup portion determines whether or not to complete imaging. When it is determined to complete imaging, imaging and tracking are completed. When it is determined not to complete imaging, the process returns to Step S105 so as to continue imaging and tracking.

As described above, in this embodiment, the moving amount can be determined by simple calculation without adding an optical system to the LSLO apparatus. Therefore, the eye movement can be measured at high speed, and further, the moving amount thereof can be fed back to the OCT apparatus.

(Third Embodiment; AO-SLO Optical System)

A third embodiment of the present invention is hereinafter described.

In this embodiment, similarly to the first and second embodiments, the fundus image is acquired, and intersection points between the radiation beam and a plurality of blood vessels are extracted. After that, the fundus movement is calculated, and then the positions to be extracted are changed so as to calculate the fundus movement. Further, the fundus movement value is fed back to an AO-SLO optical system (referred to also as an AO-SLO apparatus) in which an adaptive optics (AO), which is a compensation optical system for measuring eye aberration and correcting the aberration, is incorporated in the optical system, and hence a high quality SLO image can be acquired. Note that, the AO-SLO optical system is exemplified as one of the second optical system in the present invention.

(Entire Structure of Apparatus)

A structure of the fundus image pickup apparatus of this embodiment is described with reference to FIG. 8.

A fundus image pickup apparatus 301 in this embodiment is formed of an AO-SLO image pickup portion and an SLO image pickup portion. The AO-SLO image pickup portion acquires a fundus image having a narrow angle of view at high resolution, and the other SLO image pickup portion acquires a fundus image having a wide angle of view as an observation image for acquiring the fundus image by the AO-SLO image pickup portion. In this embodiment, the AO-SLO image pickup portion acquires an image having an angle of view corresponding to an area of 0.6 mm×0.6 mm on the fundus at a resolution of 6 μm, and the SLO image pickup portion acquires an image having an angle of view corresponding to an area of 8 mm×8 mm at a resolution of 16 μm. Individual structures are hereinafter described in detail. The SLO image pickup portion is the same as that of the first embodiment except for a part. In FIG. 8, the same components are denoted by the same symbols as those in FIG. 1 of the first embodiment or in FIG. 6 of the second embodiment.

Figure 8:
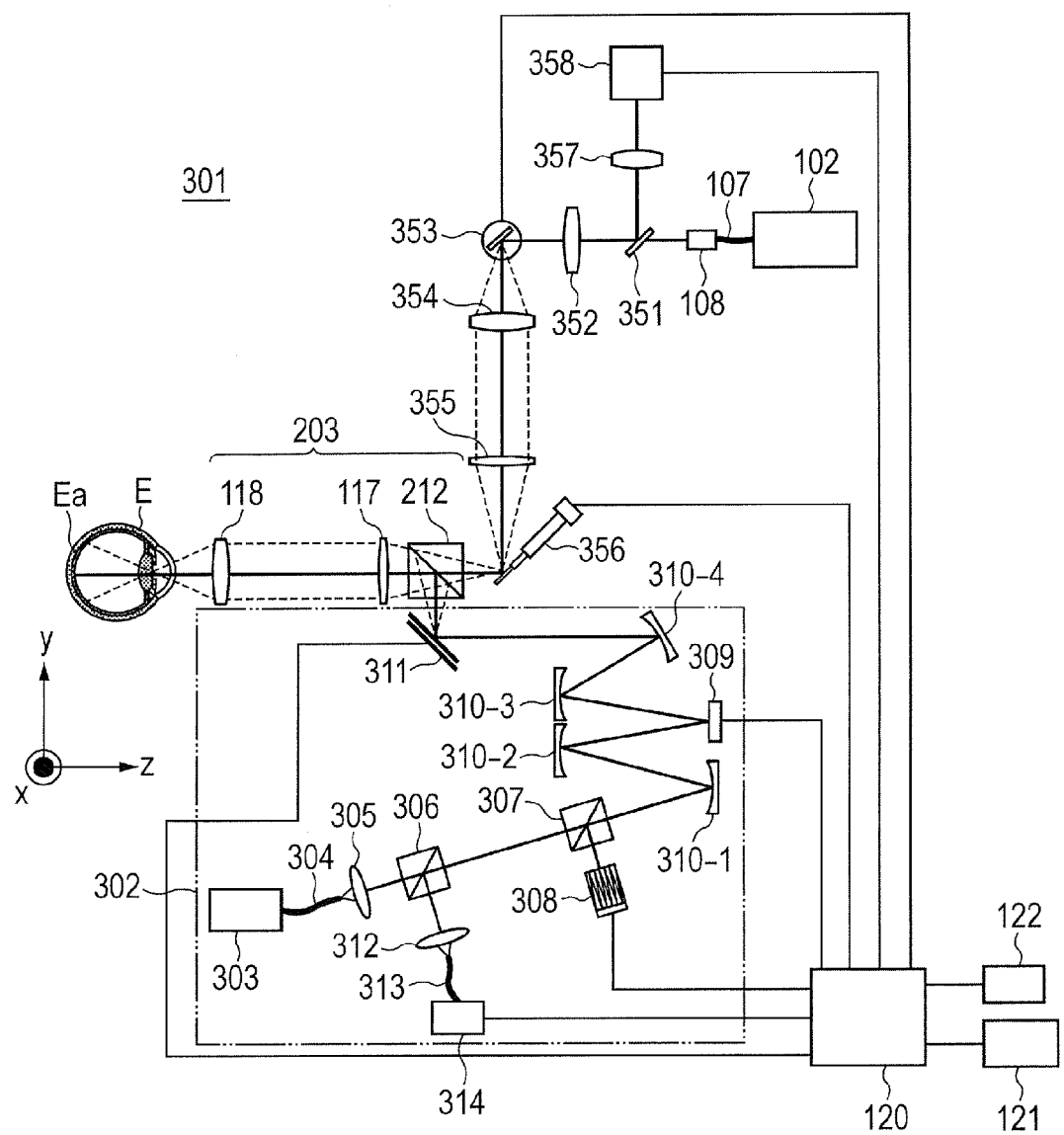
FIG. 8 is a schematic diagram of a structure of a fundus image pickup apparatus according to a third embodiment of the present invention.

The AO-SLO image pickup portion in this embodiment is formed of an AO-SLO portion 302 enclosed by a double dot dashed line and the ocular optical system 203 in FIG. 8. As a light source 303, an SLD light source having a wavelength of 840 nm is used. In this embodiment, the light source is shared between taking of a fundus image and wavefront measurement, but it is possible to use different light sources and to combine the waves on the way.

The light emitted from the light source 303 propagates in an optical fiber 304 and is radiated as collimated measuring light by a collimator 305. The radiated measuring light passes through a beam splitter 306 and is guided to the compensation optical system.

The compensation optical system includes a beam splitter 307, a wavefront sensor 308 for measuring aberration, a wavefront correction device 309, and reflection mirrors 310-1 to 310-4 for guiding the light thereto. The reflection mirrors 310-1 to 310-4 are disposed so that the pupil of the eye to be inspected E is optically conjugate with at least the wavefront sensor 308 and the wavefront correction device 309. In addition, in this embodiment, a spatial phase modulator using a liquid crystal element is used as the wavefront correction device 309.

The measuring light enters the wavefront correction device 309 and is reflected so as to exit toward the reflection mirror 310-3. In the same manner, the light returning from the fundus Ea of the eye to be inspected E also enters the wavefront correction device 309 so as to exit toward the reflection mirror 310-2.

In addition, the measuring light is deflected for scanning in a two-dimensional manner by a scanning device 311. In this embodiment, a high speed resonant scanner is used for the X direction (main scanning), and a galvano scanner is used for the Y direction (sub-scanning), as the scanning device 311.

The measuring light deflected for scanning by the scanning device 311 is reflected by the beam splitter 212, passes through the scan lens 117 and the ocular lens 118, and enters the eye to be inspected E. The measuring light having entered the eye to be inspected E is reflected or scattered by the fundus Ea and propagates along the same optical path. A part of the measuring light enters the wavefront sensor 308 via the beam splitter 307. The wavefront sensor 308 measures a wavefront of a light beam, and a Shack-Hartmann sensor is used as the wavefront sensor 308.

A part of the reflected or scattered light having passed through the beam splitter 307 is reflected by the beam splitter 306 this time and is guided to a light intensity sensor 314 formed of an avalanche photodiode via a collimator 312 and an optical fiber 313. The light intensity sensor 314 converts the light into an electric signal, which is processed by the control portion 120. Then, the control portion 120 controls the X direction (main scanning) resonant scanner and the Y direction (sub-scanning) galvano scanner of the scanning device 311 to rotate by very small angles, and hence light intensity information from the target region of the fundus is obtained. Thus, the image is formed as a fundus image and is displayed on the monitor 121.

In addition, the wavefront sensor 308 and the wavefront correction device 309 are connected to the control portion 120. The control portion 120 calculates a modulation amount (correction amount) for correcting the wavefront acquired as a measurement result of the wavefront sensor 308 into a wavefront without aberration and instructs the wavefront correction device 309 to perform the modulation. The wavefront measurement and the instruction to the wavefront correction device 309 are repeatedly performed, and feedback control is performed so as to always keep an optimal wavefront. In this embodiment, as the wavefront correction device 309, a reflection type liquid crystal spatial phase modulator having the number of pixels of 600×600 is used.

Next, a structure of the SLO image pickup portion is described with reference to the same diagram of FIG. 8. The same symbols as those in FIG. 1 or FIG. 6 denote the same components of the first embodiment or the second embodiment.

As the light source 102, a semiconductor laser having a wavelength of 760 nm is used. The laser beam emitted from the laser light source 102 propagates in the fiber 107 and exits as a collimated beam from the fiber collimator 108. The exiting beam passes through a perforated mirror 351, a lens 352, a Y direction SLO scanner 353, and relay lenses 354 and 355 so as to be guided to an X direction SLO scanner 356. Further, the beam passes through the beam splitter 212 of the ocular optical system 203, the scan lens 117, and the ocular lens 118 so as to enter the eye to be inspected E. Here, a resonant scanner is used for the X direction SLO scanner 356, and a galvano scanner is used for the Y direction SLO scanner 353. In addition, the direction of rotating the X direction SLO scanner 356 is a main scanning direction of the SLO, and the direction of rotating the Y direction SLO scanner 353 is a sub-scanning direction of the SLO. Note that, the X direction SLO scanner 356 and the Y direction SLO scanner 353 are illustrated in directions different from those in reality for description.

The beam having entered the eye to be inspected E is radiated as a point-like beam to the fundus Ea of the eye to be inspected E. This beam is reflected or scattered by the fundus Ea, propagates along the same optical path, and returns to the perforated mirror 351. Among the light rays reflected or scattered by the fundus Ea, light rays passing through the peripheral portion of the pupil are reflected by the perforated mirror 351, pass through a lens 357, and are received by a light intensity sensor 358 formed of an avalanche photodiode. Information of intensity detected by the light intensity sensor 358 is transmitted to the control portion 120 and is processed so that the fundus image is generated.

The control portion 120 is connected to, in addition to the light intensity sensor 358, the Y direction SLO scanner 353, the X direction SLO scanner 356, the input device 122 for the inspector to perform the input operation, and the monitor 121 for displaying the generated fundus image and a display for the input operation.

When the control portion 120 controls the X direction SLO scanner 356 and the Y direction SLO scanner 353 to rotate by very small angles, the radiation beam scans the fundus Ea so that a two-dimensional fundus image is acquired. The control portion 120 controls the monitor 121 to display the fundus image.

(Eye Movement Measurement)

Unlike the first embodiment, the SLO of this embodiment radiates a point-like beam to the fundus Ea, and the beam is deflected for main scanning in the X direction and is deflected for sub-scanning in the Y direction. However, it is possible to regard the main scanning as one line, and to consider that the line beam L0 in FIG. 2A of the first embodiment scans in the Y direction.

Therefore, similarly to the first embodiment, the inspector moves the cursor 123, which is displayed on the fundus image on the monitor 121 and which is illustrated in FIG. 2B, in the Y axis direction by operating the input device 122 while viewing the fundus image. Then, the cursor 123 is fixed at a position where a plurality of blood vessels on the fundus cross the cursor 123, three blood vessels having high contrast are not parallel to each other, and the blood vessels do not branch in the vicinity.

Figure 9:
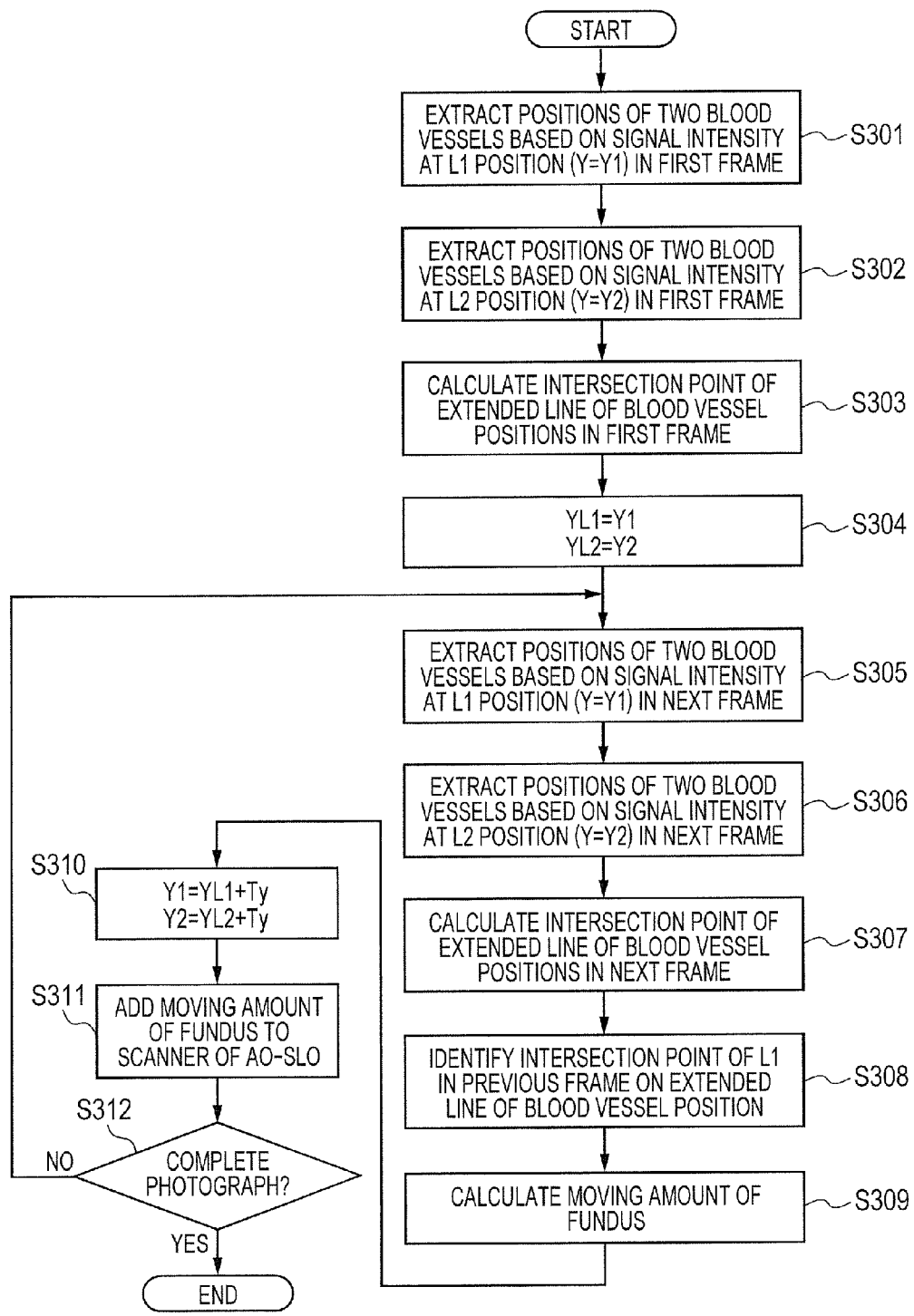
FIG. 9 is a flowchart according to the third embodiment.
Figure 10:
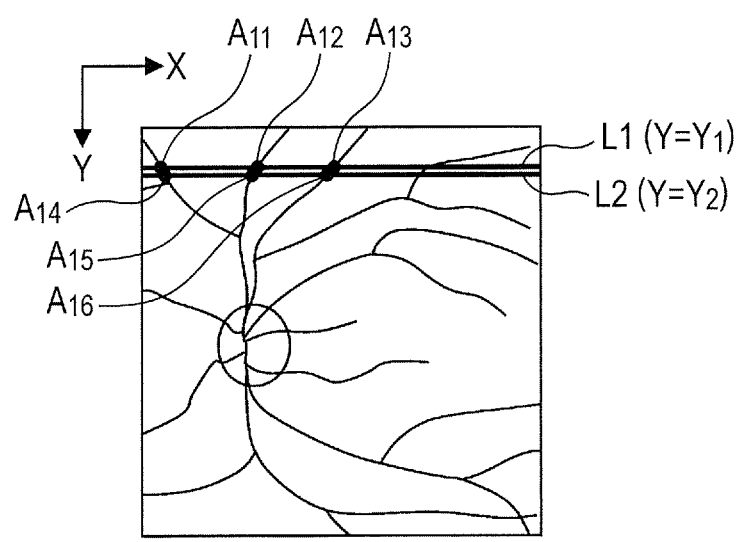
FIG. 10 is an explanatory diagram of procedure according to the third embodiment.

When the cursor 123 is fixed by an input from the inspector, the control portion 120 starts to measure the fundus movement. FIG. 9 illustrates a procedure flow of this detection. First, in Step S301, the first frame that is the latest frame at that time, namely the first area scanning is used. As illustrated in FIG. 10, the X positions of the intersection points between the line L1 at the position where the cursor 123 is fixed, namely the line at $Y=Y_1$ and center portions of three blood vessels having large signal intensity of the light intensity sensor 358 are identified. The intersection points between the line and the center portions of the three blood vessels are represented by $A_{11}, A_{12}$, and $A_{13}$, and coordinates thereof are expressed by $(X_{11}, Y_1)$, $(X_{12}, Y_1)$, and $(X_{13}, Y_1)$.

Next, in Step S302, as illustrated in FIG. 10, the X positions of the intersection points between the line L2 apart from the line L1 at the position where the cursor 123 is fixed by 6 pitches in the Y direction, namely the line at $Y=Y_2$ and the same three blood vessels having large signal intensity as in Step S301 are identified in the same manner. The intersection points between the line and the center portions of the three blood vessels are represented by $A_{14}, A_{15}$, and $A_{16}$, and coordinates thereof are expressed by $(X_{14}, Y_2)$, $(X_{15}, Y_2)$, and $(X_{16}, Y_2)$. The above-mentioned positions of the lines L1 and L2 are the first and second scanning positions, and the positions $(X_{11}, Y_1)$, $(X_{12}, Y_1)$, $(X_{13}, Y_1)$, $(X_{14}, Y_2)$, $(X_{15}, Y_2)$, and $(X_{16}, Y_2)$ of the blood vessels crossing the lines are the first blood vessel positions. Note that, because a diameter of the radiation beam on the fundus is approximately 16 μm, a height of the line in the X axis direction on a standard fundus is approximately 16 μm. In addition, because a data acquiring pitch for image generation is also 16 μm, 6 pitches correspond to 100 μm.

Step S303 is the same as Step S103 in the first embodiment. Based on the above-mentioned intersection points in the first frame, positions of an intersection point $A_{17}$ $(X_{17}, Y_{17})$ between an extended line of a line segment $A_{11}$-$A_{14}$ and an extended line of a line segment $A_{12}$-$A_{15}$, and an intersection point $A_{18}(X_{18}, Y_{18})$ between an extended line of the line segment $A_{12}$-$A_{15}$ and an extended line of a line segment $A_{13}$-$A_{16}$ are determined by applying Equations (1) and (2).

The above-mentioned fundus image of the first frame becomes a reference for the tracking described below. Therefore, in Step S304, Y coordinate values of the lines L1 and L2 in Equations (3) and (4) are stored as $YL_1$ and $YL_2$.

From Step S305, data of the next frame, namely the second area scanning, are handled. In Step S305, at the position of the line L1 ($Y=Y_1$) used in Step S301, namely at the first scanning position, similarly to Step S301, the X positions of the intersection points between the line and the center portions of the three blood vessels are identified. The intersection points between the line and the center portions of the three blood vessels are represented by $A_{21}, A_{22}$, and $A_{23}$, and coordinates thereof are expressed by $(X_{21}, Y_1)$, $(X_{22}, Y_1)$, and $(X_{23}, Y_1)$. In this embodiment, because the frame rate is 60 frames per second, the moving amount of the fundus is small, and hence the same blood vessels as in Step S301 can be extracted.

In Step S306, similarly to Step S302, the X positions of the intersection points between the line L2 and the three blood vessels illustrated in FIG. 10 are identified. The intersection points between the line and the center portions of the three blood vessels are represented by $A_{24}, A_{25}$, and $A_{26}$, and coordinates thereof are expressed by $(X_{24}, Y_2)$, $(X_{25}, Y_2)$, and $(X_{26}, Y_2)$. The above-mentioned positions $(X_{21}, Y_1)$, $(X_{22}, Y_1)$, $(X_{23}, Y_1)$, $(X_{24}, Y_2)$, $(X_{25}, Y_2)$, and $(X_{26}, Y_2)$ of the blood vessels crossing the lines L1 and L2, which are the first scanning positions, are the second blood vessel positions.

The next Step S307 is the same as Step S303. Positions of an intersection point $A_{27}(X_{27}, Y_{27})$ between an extended line of a line segment $A_{21}$-$A_{24}$ and an extended line of a line segment $A_{22}$-$A_{25}$, and an intersection point $A_{28}$ $(X_{28}, Y_{28})$ between an extended line of the line segment $A_{22}$-$A_{25}$ and an extended line of a line segment $A_{23}$-$A_{26}$ are determined by applying Equations (5) and (6). This means that the intersection points $A_{17}$ and $A_{18}$ in Step S303 have moved respectively to the intersection points $A_{27}$ and $A_{28}$ by the fundus movement.

In Step S308, moved points are identified other than the intersection points $A_{17}$ and $A_{18}$ in Step S303 and the intersection points $A_{27}$ and $A_{28}$ in Step S307. Therefore, positions which are on the extended lines of a line segment $A_{21}$-$A_{24}$, a line segment $A_{22}$-$A_{25}$, and a line segment $A_{23}$-$A_{26}$, and which intersect with the line L1 in the previous frame are determined by the following Equation (7) in the application of Equation (10).

Next, in Step S309, using Equation (11), the moving amount of the fundus is calculated. It is possible to calculate two sets of the translational movement amounts Tx and Ty and the rotational movement angle θ from the point related to the extended line of the line segment $A_{21}$-$A_{24}$ and the extended line of the line segment $A_{22}$-$A_{25}$, and from the point related to the extended line of the line segment $A_{22}$-$A_{25}$ and the extended line of the line segment $A_{23}$-$A_{26}$, by using the method of least squares. By averaging the calculated values, the translational movement amounts Tx and Ty and the rotational movement angle θ are determined. Because the intersection points between the lines L1 and L2 and the three blood vessels are used, the translational movement amounts Tx and Ty and the rotational movement angle θ can be determined at higher accuracy than the case of using the intersection points between the lines and the two blood vessels.

In Step S310, in consideration of the movement amount Ty in the Y direction of the determined translational movement amounts, the intersection points between the lines L1 and L2 and the blood vessels are determined in the next frame, and hence calculation of Equations (12) and (13) is performed. In other words, new lines L1 and L2 apart from the first and second scanning positions by the determined moving amounts in the Y direction are the third and fourth scanning positions. This corresponds to performing actual tracking of the position of the blood vessels to be extracted only in the Y direction.

In the next Step S311, the measured eye movement is fed back to the AO-SLO apparatus. In other words, the control portion 120 drives the X direction SLO scanner 356 and the Y direction SLO scanner 353 of the AO-SLO apparatus after adding the translational movement amounts Tx and Ty and the rotational movement angle θ determined in Step S309. As The translational movement amounts Tx and Ty, the scanning start positions may be shifted respectively only by amounts Tx and Ty by controlling rotations of the X direction SLO scanner 356 and the Y direction SLO scanner 353. In addition, as the rotational movement angle θ, an angle θ may be set by controlling rotation of the Y direction SLO scanner 353 in the sub-scanning.

In this embodiment, the fundus image acquired by the AO-SLO apparatus has a frame rate of 60 frames per second in the same manner as in the SLO apparatus, and the fundus movement can be tracked for each frame on the AO-SLO apparatus side.

Further, in Step S312, it is determined whether or not there is an input from the inspector to complete imaging. When there is an input, imaging and tracking are completed. When there is not any input, the process returns to Step S305 so as to continue imaging and tracking.

When Step S305 and subsequent steps are repeated, the next frame, namely an image by the third area scanning is further handled. In this case, in Steps S305 to S308, third blood vessel positions are identified, which are positions of the blood vessels crossing the above-mentioned new lines L1 and L2, namely the third and fourth scanning positions. Further, after performing the calculation of Equations (5) to (10), the moving amount of the fundus, namely the second moving amount is calculated based on the first and third blood vessel positions by using Equation (11) in Step S309.

As described above, in this embodiment, the moving amount can be determined by simple calculation without adding an optical system to the SLO apparatus. Therefore, the fundus movement can be measured at high speed, and further, the moving amount thereof can be fed back to the AO-SLO apparatus.

(Fourth Embodiment; Anterior Ocular Segment OCT Optical System)

A fourth embodiment of the present invention is hereinafter described.

In this embodiment, the image of the anterior ocular segment is acquired, the intersection points between the radiation beam and a plurality of blood vessels on the conjunctiva are extracted, and then the eye movement is calculated. After that, the position for extraction is changed, and the fundus movement is calculated. Further, a value of the eye movement is fed back to the OCT optical system for anterior ocular segment (referred to also as an anterior ocular segment OCT apparatus), and hence a high quality OCT image (a tomographic image or a three-dimensional image having little positional shift) is acquired.

(Entire Structure of Apparatus)

Figure 11:
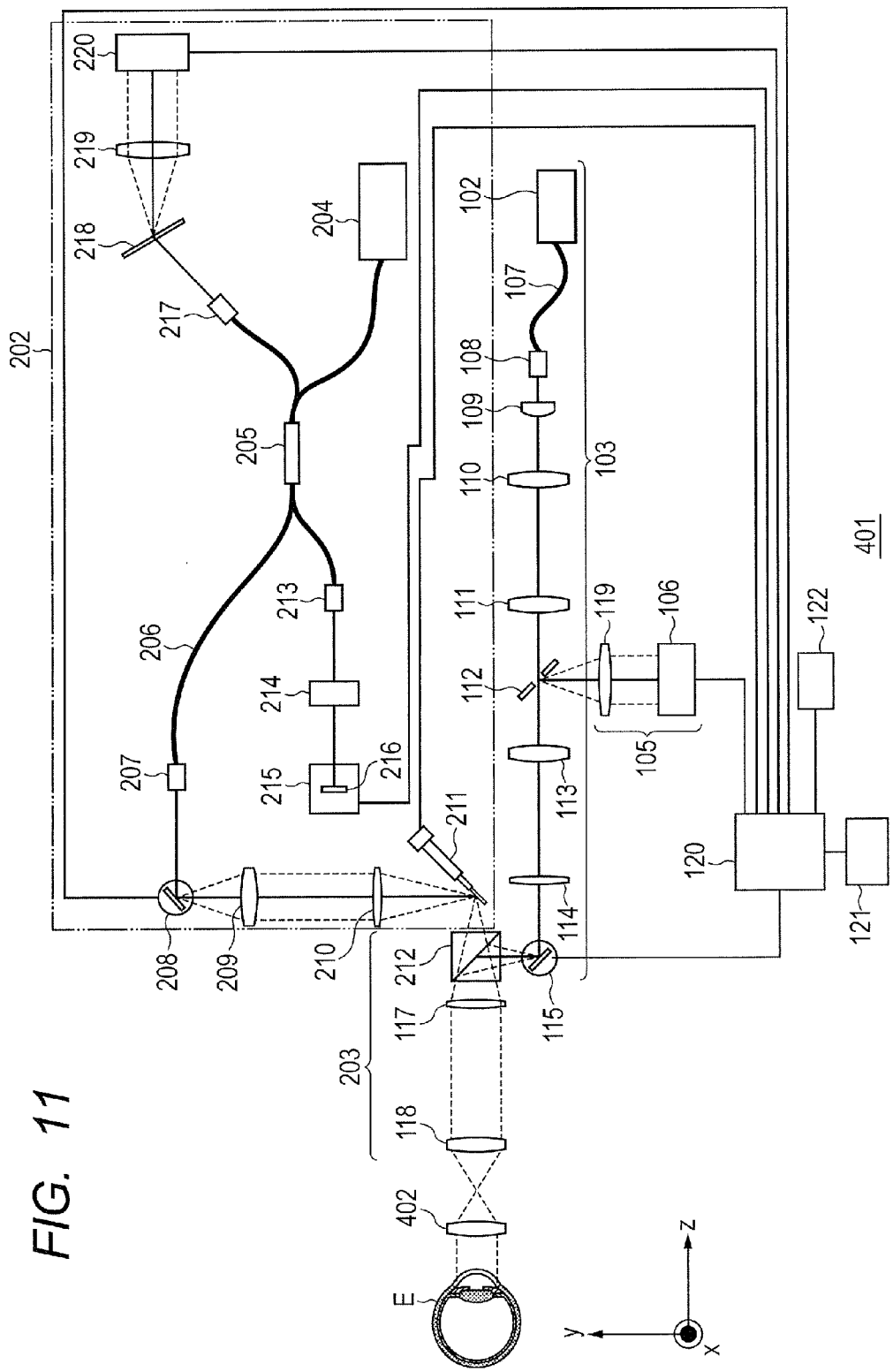
FIG. 11 is a schematic diagram of a structure of an anterior ocular segment image pickup apparatus according to a fourth embodiment of the present invention.

A structure of an anterior ocular segment image pickup apparatus of this embodiment is described with reference to FIG. 11.

An anterior ocular segment image pickup apparatus 401 of this embodiment has a structure in which a lens 402 is added to the fundus image pickup apparatus 201 of FIG. 6 of the second embodiment. Other than the lens 402, components and their symbols are the same, and therefore description thereof is omitted. However, it is necessary to read "fundus" and "fundus image" in the description of the second embodiment as "anterior ocular segment" and "anterior ocular segment image". Note that, it is possible to adopt a structure in which the lens 402 is insertable and removable into and from the optical path so that imaging of the anterior ocular segment and imaging of the fundus can be switched. In addition, it is possible to adopt a structure in which the optical members for taking an anterior ocular segment image, which include the lens 402, can be inserted or removed into or from the apparatus, and the user attaches the optical members to the apparatus when it is necessary to take an anterior ocular segment image. In other words, the image pickup apparatus according to the fourth embodiment of the present invention includes the lens 402 as an example of the optical member to be disposed between the scanner as the scanning unit and the eye to be inspected, and changes an irradiation position of the measuring light to the eye to be inspected between the fundus and the anterior ocular segment.

(Eye Movement Measurement)

Figure 12:
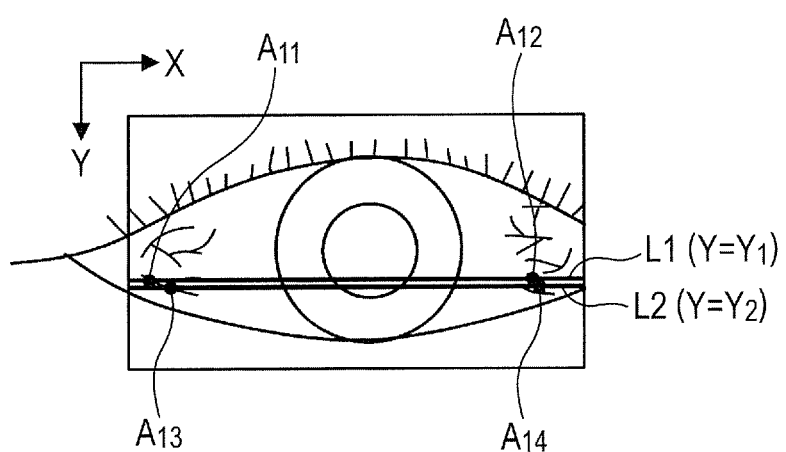
FIG. 12 is an explanatory diagram of procedure according to the fourth embodiment.

FIG. 12 illustrates an example of the anterior ocular segment image acquired as described above, the lines L1 and L2 for blood vessel extraction, and the intersection points $A_{11}$, $A_{12}$, $A_{13}$, and $A_{14}$ of the extracted blood vessels.

Figure 13:
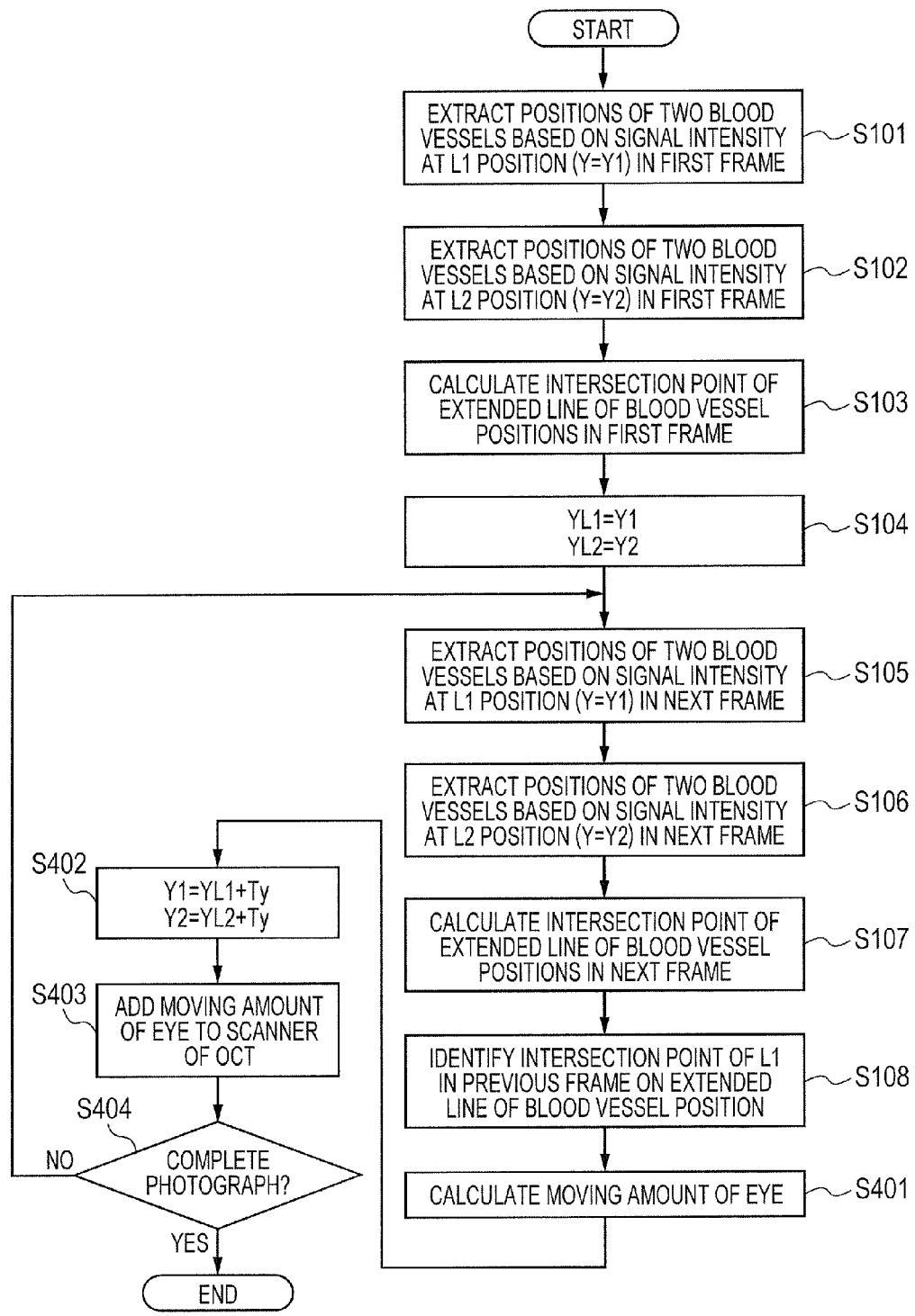
FIG. 13 is a flowchart according to the fourth embodiment.

Similarly to the second embodiment, when the cursor 123 is fixed by an input from the inspector, the control portion 120 starts to detect the anterior ocular segment movement. FIG. 13 illustrates a flow of this detection. Steps S101 to S108 are the same as in the first embodiment, and hence description thereof is omitted. However, the extraction target is a blood vessel of the conjunctiva.

In the next Step S401, the eye moving amount is calculated. Equation (11) is used, and the calculation method is the same as that of the first embodiment.

In Step S402, in consideration of the movement amount Ty in the Y direction of the determined translational movement amount, the intersection points between lines L1 and L2 and the blood vessels are determined in the next frame. Therefore, calculation of Equations (12) and (13) is performed. In other words, new lines L1 and L2 apart from the first and second scanning positions by the determined moving amounts in the Y direction are the third and fourth scanning positions. This corresponds to performing actual tracking of the position of the blood vessels to be extracted only in the Y direction.

In Step S403, the measured eye movement is fed back to the OCT apparatus. In other words, the control portion 120 drives the Y direction OCT scanner 208 and the X direction OCT scanner 211 of the OCT apparatus after adding the translational movement amounts Tx and Ty and the rotational movement angle θ determined in Step S401. As the translational movement amounts Tx and Ty, scanning start positions may be shifted respectively by amounts Tx and Ty by controlling rotations of the X direction OCT scanner 211 and the Y direction OCT scanner 208. In addition, as the rotational movement angle θ, an angle θ may be set by controlling rotation of the Y direction OCT scanner 208 in the sub-scanning.

A B-scan image that is an anterior ocular segment OCT tomographic image usually has a frame rate of 30 to 150 frames per second although depending on a speed of the line sensor and the number of pixels of the image, and the frame rate of the LSLO may correspond thereto.

Further, in Step S404, the OCT image pickup portion determines whether or not to complete imaging. When it is determined to complete imaging, imaging and tracking are completed. When it is determined not to complete imaging, the process returns to Step S105 so as to continue imaging and tracking.

When Step S105 and subsequent steps are repeated, the next frame, namely an image by the third area scanning is further handled. In this case, in Steps S105 to S108, third blood vessel positions are identified, which are positions of the blood vessels crossing the above-mentioned new lines L1 and L2, namely the third and fourth scanning positions. Then, calculation of Equations (5) to (10) is performed. After that, the moving amount of the fundus, namely the second moving amount is calculated based on the first and third blood vessel positions by using Equation (11) in Step S401.

As described above, also in this embodiment, the moving amount can be determined by simple calculation without adding an optical system to the LSLO apparatus. Therefore, the movement of the anterior ocular segment can be measured at high speed, and further, the moving amount thereof can be fed back to the anterior ocular segment OCT apparatus.

In addition, it is also possible to use the OCT apparatus both in the anterior ocular segment acquiring mode for acquiring an image of the anterior ocular segment and in the fundus mode for acquiring an image of the fundus. In this case, it is preferred that the control portion 120 include a module region functioning as an acquired portion switching unit for switching the characteristic portion to be acquired between the characteristic portion in the fundus image and the characteristic portion in the anterior ocular segment image in accordance with the image acquiring mode when the position acquiring unit acquires a plurality of positions of the blood vessels.

(Other Embodiments)

In the embodiments described above, the OCT image pickup portion and the AO-SLO image pickup portion are used as an apparatus for feeding back the eye movement, but it is possible to use an ophthalmologic apparatus for confrontation field test or blood flow measurement. In addition, the ophthalmologic apparatus performs eye movement correction in real time, but it is possible to store the movement data so as to perform alignment of the image and measured positions after finishing the eye movement measurement.

In addition, in the embodiments described above, the inspector determines the position of the cursor 123 to start the eye movement measurement. It is possible to automatically start the eye movement measurement by automatically fixing the cursor by general image processing at a position where a plurality of blood vessels to be extracted are not parallel to each other and where there is no blanch of the blood vessels to be extracted in the vicinity by a predetermined distance.

Further, the eye movement is measured in each frame in the embodiments described above, but it is possible to measure each plurality of frames if it is not necessary to measure at high speed. In addition, in this case, it is possible not to scan the entire frame to be measured but to scan only a part to be used for measurement so that measurement time can be shortened. In addition, line scanning is described in the embodiments described above, but it is possible to measure the eye movement of the eye to be inspected by using a point scanning type of scanning unit as long as the scanning unit can scan at high speed so as to support the involuntary eye movement of the eye to be inspected. In this case, it is preferred in a raster scan to measure the eye movement of the eye to be inspected by using two main scanning lines separated from each other by a predetermined distance among a plurality of main scanning lines. In addition, it is preferred in a radial scan to measure the eye movement of the eye to be inspected by using two scanning lines separated from each other by a predetermined distance among a plurality of crossing scanning lines. In addition, it is preferred in a circle scan to measure the eye movement of the eye to be inspected by using two scanning circles separated from each other by a predetermined distance among a plurality of concentric scanning circles.

Further, the present invention is also implemented by executing the following process. Specifically, in this process, software (program) for implementing the functions of the above-mentioned embodiments is supplied to a system or an apparatus via a network or various kinds of storage medium, and a computer (CPU, MPU, or the like) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-006011, filed Jan. 16, 2012, which is hereby incorporated by reference herein in its entirety.

What is claimed is:

1. An ophthalmologic image pickup apparatus which includes a first optical system having a first scanning unit and a second optical system having a second scanning unit, a part of the second optical system being the same as a part of the first optical system, for acquiring a first fundus image of an eye to be inspected and a second fundus image of the eye to be inspected acquired at a different time from the first fundus image, based on return light from the eye to be inspected which is irradiated with measuring light via the first scanning unit, the ophthalmologic image pickup apparatus comprising:
   an extracting unit configured to extract a first blood vessel and a second blood vessel in the first fundus image, and to extract a plurality of blood vessels corresponding to the first blood vessel and the second blood vessel in the second fundus image;
   a position acquiring unit configured to acquire coordinates of a plurality of positions including (1) intersection positions between (a) a first scanning line image generated by the first scanning unit in the first fundus image and (b) the extracted first blood vessel and second blood vessel, (2) intersection positions between (a) a second scanning line image generated by the first scanning unit in the first fundus image and (b) the extracted first blood vessel and second blood vessel, and (3) intersection positions between (a) a plurality of scanning line images generated by the first scanning unit in the second fundus image and (b) the extracted plurality of blood vessels;
a measuring unit configured to measure movement of the eye to be inspected based on the coordinates of the plurality of positions; and
a control unit for controlling the second scanning unit based on the measured movement.

2. An ophthalmologic image pickup apparatus according to claim 1, wherein the position acquiring unit acquires positions of the first blood vessel and the second blood vessel crossing a third scanning line and a fourth scanning line which are separated from the first scanning line and the second scanning line by the measured moving amount, and
wherein the measuring unit measures the movement of the eye to be inspected based on the acquired positions on the first blood vessel and the second blood vessel.

3. An ophthalmologic image pickup apparatus according to claim 1, wherein the position acquiring unit acquires a position of a third blood vessel from the first scanning line image in the first fundus image of the eye to be inspected, and a position of the third blood vessel from the second scanning line image, and acquires the position of the third blood vessel from the first scanning line image and the second scanning line image in the second fundus image acquired at the different time from the first fundus image, and
wherein the measuring unit measures the movement of the eye to be inspected based on the position of any one of the first blood vessel and the second blood vessel and the position of the third blood vessel in the first image and the second image.

4. An ophthalmologic image pickup apparatus according to claim 1, wherein the first blood vessel and the second blood vessel have different gradients in the first fundus image.

5. An ophthalmologic image pickup apparatus according to claim 1, wherein the first blood vessel is nonparallel to the second blood vessel in the first fundus image.

6. An ophthalmologic image pickup apparatus according to claim 1, further comprising an optical member to be disposed between the first scanning unit and the eye to be inspected, the optical member being configured to change an irradiation position of the measuring light with respect to the eye to be inspected.

7. An ophthalmologic image pickup apparatus according to claim 1, wherein the second optical system comprises at least one of an AO-SLO optical system and an OCT optical system.

8. An ophthalmologic image pickup apparatus according to claim 1, wherein the first optical system includes an optical member for shaping the measuring light into a line shape.

9. An ophthalmologic image pickup apparatus according to claim 1, further comprising:
a display control unit configured to control a display unit to display the image of the eye to be inspected in real time; and
a designation unit configured to designate a position corresponding to one of the plurality of scanning lines by using a linear display form on the image of the eye to be inspected.

10. An ophthalmologic image pickup apparatus according to claim 9, further comprising a determining unit configured to determine a position apart from the designated position of the one of the plurality of scanning lines by a predetermined distance as a second scanning line position.

11. An ophthalmologic image pickup apparatus according to claim 1, wherein the measuring unit measures at least one of translational movement and rotational movement of the eye to be inspected as the movement of the eye to be inspected.

12. A method of controlling an ophthalmologic image pickup apparatus which includes a first optical system having a first scanning unit and a second optical system having a second scanning unit, a part of the second optical system being the same as a part of the first optical system, for acquiring a first fundus image of an eye to be inspected and a second fundus image of the eye to be inspected acquired at a different time from the first fundus image, based on return light from the eye to be inspected which is irradiated with measuring light via the first scanning unit, the method comprising:
extracting a first blood vessel and a second blood vessel in the first fundus image, and extracting a plurality of blood vessels corresponding to the first blood vessel and the second blood vessel in the second fundus image;
acquiring coordinates of a plurality of positions including (1) intersection positions between (a) a first scanning line image generated by the first scanning unit in the first fundus image and (b) the extracted first blood vessel and second blood vessel, (2) intersection positions between (a) a second scanning line image generated by the first scanning unit in the first fundus image and (b) the extracted first blood vessel and second blood vessel, and (3) intersection positions between (a) a plurality of scanning line images generated by the first scanning unit in the second fundus image and (b) the extracted plurality of blood vessels;
measuring movement of the eye to be inspected based on the coordinates of the plurality of positions; and
controlling the second scanning unit based on the measured movement.

13. A program for causing a computer to perform the steps of the method of controlling an ophthalmologic image pickup apparatus according to claim 12.

* * * * *